United States Patent [19]

Hackl et al.

[11] Patent Number: 4,987,081
[45] Date of Patent: Jan. 22, 1991

[54] CHEMICAL/BIOLOGICAL PROCESS TO OXIDIZE MULTIMETALLIC SULPHIDE ORES

[75] Inventors: Ralph P. Hackl; Frank R. Wright; Albert Bruynesteyn, all of North Vancouver, Canada

[73] Assignee: GB Biotech Inc., British Columbia, Canada

[21] Appl. No.: 172,278

[22] Filed: Mar. 23, 1988

Related U.S. Application Data

[62] Division of Ser. No. 71,968, Jul. 10, 1987, Pat. No. 4,888,293.

[51] Int. Cl.$^5$ .............................................. C01G 28/00
[52] U.S. Cl. ................................. 435/262; 435/252.4; 435/282; 435/818; 423/DIG. 17
[58] Field of Search ...................... 425/282, 262, 252.4, 425/243, 818, 819; 423/DIG. 17; 75/6; 44/622, 625

[56] References Cited

U.S. PATENT DOCUMENTS

| | | |
|---|---|---|
| 2,147,004 | 2/1939 | Chapman . |
| 2,234,140 | 3/1941 | Falconer . |
| 2,315,187 | 3/1943 | Chapman et al . |
| 2,829,964 | 4/1958 | Zimmerley et al. ................ 435/262 |
| 3,266,889 | 8/1966 | Duncan ............................... 435/262 |
| 3,305,353 | 2/1967 | Duncan ....................... 423/DIG. 17 |
| 3,330,650 | 7/1967 | Zimmerley et al. . |
| 3,347,661 | 10/1967 | Mayling ....................... 423/DIG. 17 |
| 3,574,600 | 4/1971 | Scheiner et al. . |
| 3,607,235 | 9/1971 | Duncan et al. . |
| 3,639,925 | 2/1972 | Scheiner et al. . |
| 3,679,397 | 7/1972 | O'Connor ....................... 435/262 X |
| 3,796,308 | 3/1974 | McIlhinney et al. ....... 423/DIG. 17 |
| 3,846,124 | 11/1974 | Guay . |
| 3,856,913 | 11/1974 | McElroy et al. . |
| 4,038,362 | 2/1974 | Guay . |
| 4,206,288 | 6/1980 | Detz ..................................... 435/282 |
| 4,269,699 | 5/1981 | McGready et al. . |
| 4,440,644 | 4/1984 | Mudder et al. . |
| 4,461,834 | 7/1984 | Mudder et al. . |
| 4,497,778 | 2/1985 | Pooley . |
| 4,571,187 | 2/1986 | Bruynesteyn et al. . |
| 4,571,387 | 2/1986 | Bruynesteyn ....................... 435/262 |
| 4,732,608 | 3/1988 | Emmett, Jr. et al. ................ 435/262 |
| 4,748,118 | 5/1988 | Rawlings et al. . |

FOREIGN PATENT DOCUMENTS

| | | |
|---|---|---|
| 27867 | of 1977 | Australia . |
| WO02355 | of 1984 | Australia . |
| 1152754 | 8/1983 | Canada . |
| 0004431 | 10/1979 | European Pat. Off. ............ 435/262 |
| 3097369 | 11/1982 | United Kingdom . |

OTHER PUBLICATIONS

Deepak et al, J. Chem. Tech. Biotechnol., vol. 31, No. 6, (1981) pp. 358–362.
Norris et al, FEMS Microbiology Letters, 4, (1978), pp. 143–146.
Buchanan R. E. and N. E. Gibbons, 1974. Bergey's Manual of Determinative Bacteriology. The Williams and Wilkins Co. Baltimore 1268 p.
Tuovinen, O. H. and D. P. Kelly 1973, Studies on the Growth of *Thiobacillus ferrooxidans*. I. Arch. Microbiol. 88'285-298.
Lui, Ming-Shen, 1973, Oxygen transfer in a fermentor. Ph.D. thesis, Dept. Chem., Eng. U.BC.
Tomizuka, N. M. Yagisawa, J. Somaya and Y. Takahara. 1976. Continuous leaching of uranium by *Thiobacillus ferrooxidans* Argi. Biol. Chem. 40(5)'1019–1025.
Golomzik A. I. and V. I. Ivanov. 1964, Adaptation of *T. ferrooxidans* to increased hydrogen ion and iron concentrations, *Mikrobiologya* 34 No. 3:465–468.
Bruynesteyn A., Vizsolyi, A. and R. vos. 1980, The effect of low pH on the rate of ferrous iron oxidation by Thiobacillus ferrooxidans. Presented at the conference: *Use of microorganisms in Hydrometallurgy*, Pecs. Hungary.
Bruynesteyn, A. and A. Vizsolyi, 1981. The effect of pH and Eh on the chemical and biological leaching of a pyritic uranium ore, 2nd SME-SPE *International Solution Mining Symposium*, Denver, Colo.
Groudev, S. N. 1983, Participation of *Thiobacillus thiooxidans* in the leaching of metals from sulphide miner- (List continued on next page.)

Primary Examiner—Sam Rosen
Attorney, Agent, or Firm—Nixon & Vanderhye

[57] ABSTRACT

This application relates to an improved method for oxidizing multimetallic sulphide ores and concentrates, using a combination chemical/biological leaching process and at least three different types of bacteria. The treatment process for multi-metallic ores such as arsenopyrite can be made to work rapidly and to as much as 98% sulphide oxidation, when the finely ground ore or concentrate is leached in agitated, air sparged tanks, with strains of three different bacteria, *T. thiooxidans*, *T. ferrooxidans*, and *Leptospirillum ferrooxidans*. *L. ferrooxidans* is quite similar to *T. ferrooxidans* and obtains its energy for growth from the oxidation of ferrous iron. The process of the invention may conveniently be a continuously operating process utilizing more than one stage. Most of the chemical/biological action using the bacterium *T. thiooxidans* preferably takes place in the first stage, while in the subsequent stages the activity of *T. thiooxidans* is decreased in favour of the activity of the bacteria *T. ferrooxidans* and *L. ferrooxidans*, which oxidize the by then more readily available sulphide portion of the pyrite minerals present in most arsenopyrite ores and concentrates. According to the invention, bacterial cultures of *T. thiooxidans*, *T. ferrooxidans* and *L. ferrooxidans* used are first adapted to high dissolved arsenic concentrations and low pH by subjecting the cultures in a solution containing dissolved arsenic, to successive incremental concentrations of arsenic while operating in a continuous mode.

20 Claims, No Drawings

OTHER PUBLICATIONS als. Presented at: *Fifth International symposium on Biohydrometallurgy,* Cagliari, Italy.

Norris, P. R., 1903. Iron and Mineral Oxidation with leptospirillum-like bacteria. Presented at: *Fifth International Symposium on Biohydrometallurgy,* Cagliari, Italy.

Brown, J. E., Luong, H. V. and J. M. Forshaug 1982. The occurrence of *Thiobacillus ferrooxidans* and arsenic in subarctic streams affected by gold-mine drainage, *Arctic* 35 No. 3:417–421.

E. Livesey-Goldblatt, Philippe Norman, P. and D. R. Livesey-Goldblatt, "Gold recovery from Arsenopyrite/-pyrite ore by Bacterial Leaching and Cyanidation", Presented at: *Fifth International Symposium on Biohydrometallurgy,* Cagliara, Italy.

Karavaiko, G. I., Chuchalin, L. K. and T. A. Pivovarova, 1985, Microbiological leaching of metals from arsenopyrite containing concentrates, Presented at: *Sixth International Symposium on Biohydrometallurgy,* Vancouver, Canada.

General Mining Corporation, "Plasmid vectors resistant to arsenic-capable of replication in *Thiobacillus ferrooxidans*", RSA No. 8406735.

D. A. Rawlings, I. Pretorius and D. R. Woods, 1984, "Expression of a *Thiobacillus ferrooxidans* origin of replication in *Escherichia coli*", J. of Bacteriology, vol. 158, No. 2:737–738.

Norris, P. R. and Kelley, P. D. 1982, The use of mixed microbial cultures in metal recovery, *Microbial Interaction and Communities,* A. T., Bell and J. H. Slater (eds), Academic Press. London, 1, pp. 443–474.

Ehrlich, H. L. 1964, Bacterial oxidation of arsenopyrite and enargite, *Econ. Geol.* vol. 59 pp. 1306–1312.

Bos. P. and J. G. Kuenen, 1983, Microbiology of sulphur oxidizing bacteria, Proceedings of conference by The National Physical laboratory and The Metals Society, NPL Teddington, Mar. 8–10, 1983. The metals Society, London.

Karavaiko, G. I. and S. A. Mosniakova, 1974. Oxidaton of sulphide minerals by *Thiobacillus thiooxidans, Microbiologiya* 43:156–158.

CIM bulletin, Sep. 1983, B. C. Research publication, R. Lawrence & A. Bruynesteyn, "Biological Pre-oxidation to enhance gold and silver recovery from refractory pyrite ores and concentrates".

Giant Bay Resources Ltd., Annual Report of 1986.

A. Bruynesteyn, R. P. Hackl and F. Wright—"The Biotank leach process", Gold 100, Proceedings of the International Conference on Gold vol. 2: Extractive Metallurgy of Gold, Johannesburg, SAIMM, 1986.

Ralph P. Hackl and Albert Bruynesteyn, Special Report "Mineral munching microbes" Mar. 1987.

W. E. Razzel and P. S. Trussel—"Isolation and Properties of an Iron-Ozidizing Thiobacillus" B. C. Research Council, vol. 85, 1963 U of B. C. Vancouver, Canada, Published 10-9-62—pp. 595–603.

Progress in Biohydrometallurgy, Cagliari, May 1983, pp. 627–641 "Gold Recovery from Arsenopyrite Pyrite one by bacterial leaching and cyanidation" by Giovanni Rossi and Arpad Torma (O.P.I. in Australia 23, Mar., 1984 at the CBIR0 Division of Mineral Chemistry Library, Port Melbourne).

"The Bacterial leaching of Gold Dispersed in Sulphide Minerals" English Translation of Russian Article by G. I. Karavaiko, S. I. Kuznetsov and A. I. Golonizik, published by W. Burns, Stonehouse, Eng. Techicopy Limited 1977 article p. 64 (OPI in Austria 29 Jan. 1980 at the State Library of NSW).

CHEMICAL/BIOLOGICAL PROCESS TO OXIDIZE MULTIMETALLIC SULPHIDE ORES

CROSS-REFERENCE TO RELATED APPLICATIONS

This application is a divisional of earlier application Ser. No. 07/071,968 filed July 10, 1987, now U.S. Pat. No. 4,888,293.

This application relates to an improved method for oxidizing multimetallic sulphide ores and concentrates, using a combination chemical/biological leaching process and at least three different types of bacteria.

The extraction of metals from sulphide minerals through the mediation of the bacterium *Thiobacillus ferrooxidans* has been known for many years. It appears that as much as one quarter of the copper produced in Arizona is through the biological leaching of low grade copper sulphide wastes produced from open pit copper mining operations.

At present the only other known commercial application of biological leaching is at the Denison Mine in the Elliot Lake area of Ontario, Canada, where the bacterium *T. ferrooxidans* is used to extract uranium from pyritic uranium ores.

Although biological leaching methods have been developed for the oxidation of sulphide minerals in low grade waste ores, a process taking place naturally, the kinetics of such processes are so slow that they are applied only to low value waste materials. It is not uncommon that in 10 to 15 years of leaching, only 50% extraction is obtained in such cases. However, in the laboratory, when working under optimized conditions, the kinetics of the biological leaching process can be improved several hundred thousand times. As a result of such laboratory work, Duncan et al., in U.S. Pat. No. 3,607,235, describe a biological leaching process for sulphide minerals. The metal sulphide, in finely ground form, is suspended in an acidic, air-sparged solution, maintained at a pH of 2.0, together with a culture of sulphide oxidizing bacteria, identified as *T. ferrooxidans*. Extraction in the process is a function of particle size and regrinding of the leached residue is necessary to obtain extractions in excess of 90%. McElroy et al., U.S. Pat. No. 3,856,913, describe the use of silver as a catalyst in the oxidation of the mineral chalcopyrite, again using *T. ferrooxidans*, and Bruynesteyn et al. in U.S. Pat. No. 4,571,387 describe and claim a further modification to the biological process which also uses *T. ferrooxidans* for the production of elemental sulphur from the sulphide portion of the chalcopyrite mineral.

Extensive commercial application of the biological leaching process is hampered by the fact that *T. ferrooxidans* is highly sensitive to high concentrations of hydrogen ions (low pH), and to the presence in relatively low concentrations of certain elements, such as arsenic and antimony, which have an inhibitory or toxic effect.

The effect of acidity on the activity of *T. ferrooxidans* has been researched extensively. Buchanan & Gibbon, (1), reported that *T. ferrooxidans* can grow at pH values between 1.4 and 6.0. Tuovinen et al, (2), report that *T. ferrooxidans* does not grow at pH values below 1.0, but can be adapted to oxidize ferrous iron at pH 1.3 by successive culturing in media of progressively greater acidity. Tuovinen et al point out however that during the subculturing steps, the pH of the media rises to 1.7 as a result of the acid consumption of the ferrous iron oxidation, so it is questionable whether their strain was active for any length of time at pH 1.3. Lui (3), observed the same pH rise during his experiments.

Tomizuka et al, (4), reported that, when oxidizing ferrous iron in a continuous fermentor, the optimum pH was in the range 2.3-2.7. He also showed that the specific growth rate decreased to zero at pH 0.8 and was 40% and 56% of the maximum rate at pH 1.3 and 1.5 respectively. Golomzik and Ivanov (5), used serial transfers into successively more acidic media in an attempt to adapt *T. ferrooxidans* to a low pH environment. Although they quote success in obtaining growth at pH values as low as 1.0, the rate of ferrous iron oxidation at this low pH was only 17mg/l/h. At pH 2.3, rates of 500–1,000 mg/l/h have been reported (6). Thus, the adaptations obtained were of limited significance.

Bruynesteyn et al reported (6), that *T. ferrooxidans* can be adapted, by continuous culturing techniques, to pH values as low as 1.25 while retaining its rapid ferrous iron oxidation capabilities. Bruynesteyn et al also report (7) that hydrogen ions react in a synergistic manner with uranium in causing inhibition to *T. ferrooxidans*, particularly at pH 1.6.

Thus, *T. ferrooxidans* does not oxidize ferrous iron or sulphides at pH values below 1.0. Since ferric iron is an oxidant which assists in the oxidation of mineral sulphides and since the solubility of ferric iron increases with decreasing pH, the organism's pH sensitivity prevents its use in the highly oxidative solutions formed by strong ferric sulphate in solution. Additionally, many sulphide ores and concentrates are sufficiently high in sulphide content that the biologically produced sulphuric acid lowers the pH below 1.2, effectively stopping the biological leaching process.

U.S. Pat. No. 4,497,778 to F. Pooley describes a process which overcomes some of the difficulties in biological leaching of pyritic and arsenopyritic ores and concentrates, by first subjecting the mineral to a partial roast to remove part of the contained sulphur by converting the contained pyrite to pyrrhotite. The patent claims improved extraction results from this process.

Little information is available on the pH sensitivity of *T. thiooxidans*, other than that this organism, in contrast to *T. ferrooxidans*, can oxidize elemental sulphur at pH values below 1.0. Its sensitivity to inhibitors is assumed to be similar as that of *T. ferrooxidans*. Groudev (8) has shown that *T. thiooxidans*, when growing at a pH of 2.3, is capable of oxidizing certain sulphide minerals such as zinc sulphide, nickel sulphide, and cobalt sulphide, but could not oxidize pyrite and arsenopyrite. It was not determined whether this oxidation is direct or via a chemical oxidation step. In the latter case, the bacterium is thought to oxidize the elemental sulphur resulting from the chemical oxidation of the sulphide.

Norris (9) also reports that *T. thiooxidans* does not oxidize pyrite.

*Leptospirillum ferrooxidans* is still a relatively unknown organism which is reported to be similar to *T. ferrooxidans*. Norris (9) reports that Leptospirillum oxidizes ferrous iron at pH values as low as 1.4, but cannot oxidize elemental sulphur. Norris also reports that there are some indications that Leptospirillum can oxidize pyrite as well as does *Thiobacillus ferrooxidans*.

At present, no one has been able to develop an economically viable biological treatment process for refractory ores and concentrates containing arsenic, because dissolved arsenic concentrations as low as 1,000 mg/l are toxic to the leaching bacterium, while, as stated above, at the low pH values resulting from the acid produced from the pyrite when leaching pyritic arsenopyritic ores, the activity of the bacterium is severely inhibited.

Little information on the inhibitory effect of arsenic on any of *T. ferrooxidans, Leptospirillum ferrooxidans* and *T. thiooxidans* is known, although it is believed that arsenic is inhibitory to microorganisms because it tends to replace phosphorus in the microbial enzyme systems.

Brown et al (10) report that they have found *T. ferrooxidans* in Alaskan streams in the presence of up to 0.347 mg/l dissolved arsenic.

Livesey-Goldblatt, (11) reports that he adapted a strain of *T. ferrooxidans*, in a solution of pH 1.7, to arsenic concentrations as high as 4,000 mg/l.

During the Sixth International Symposium on Biohydrometallurgy (1985), Karavaiko (12) reported that, while leaching arsenopyrite with *Thiobacillus ferrooxidans* in a solution of pH 2.0, he encountered bacterial inhibition due to arsenic concentrations in the range 10–20 g/l and iron concentrations in the range 20–40 g/l.

The potential commercial significance of the inhibition by arsenic is demonstrated by attempts to use genetic engineering techniques to construct arsenic resistant strains of *T. ferrooxidans*. A recent patent application by Gencor (13), relates to work carried out at the University of Capetown by D. E. Rawlings, I. Pretorius and D. R. Woods (14). These authors studied the arsenic resistance in a strain of *Thiobacillus ferrooxidans* found to be resistant to as much as 2,048 mg/l pentavalent arsenic per liter, and were able to isolate and replicate the relevant plasmids. However, there is no information on how much arsenic resistance can be engineered or how such resistance can be replicated in the organisms. The patent is concerned with the genetic manipulations only.

At the optimum pH value for *T. ferrooxidans* of 2.4, and at values in excess thereof, ferric iron produced during the biological leaching process from the pyrites and arsenopyrites present, has a limited solubility and tends to precipitate partly as an hydroxide. This is a waste material which is very difficult to separate from the suspension. It tends to coat mineral surfaces, thus interfering with the leaching process. Also, when leaching arsenopyritic ores, the dissolved arsenic may, at these high pH values, partly precipitate as calcium arsenate, a slightly water soluble compound which is not acceptable for disposal in tailings ponds. Therefore, it is of advantage to carry out the leach at a pH of 1.0, at which value the solubility of ferric iron is increased to more than 100 g/l, as compared to less than 1 g/l at pH 2.3. Such high concentrations facilitate the chemical oxidation of metal sulphides.

We have found that in the present invention, a combined chemical-biological treatment process for multimetallic ores such as arsenopyrite can be made to work rapidly and to as much as 98% sulphide oxidation, when the finely ground ore or concentrate is leached in agitated, air sparged tanks, with strains of three different bacteria, *T. thiooxidans, T. ferrooxidans*, and *Leptospirillum ferrooxidans*.

*Leptospirillum ferrooxidans* is quite similar to *T. ferrooxidans* and obtains its energy for growth from the oxidation of ferrous iron.

*L. ferrooxidans* has not been extensively researched yet and one of the most recent articles, published in 1983 by Dr. P. R. Norris, shows that this organism can operate in the same pH range as *T. ferrooxidans* and is not able to work at pH values below 1.3. The organism is not known to be able to oxidize sulphides or elemental sulphur, although Norris, in his paper, found that Leptospirillum-like bacteria did oxidize a pyrite substrate.

We have now found that the culture of bacteria, identified as *Lepotospirillum ferrooxidans*-like bacteria, can oxidize both ferrous iron and pyrite at pH values as low as 0.3.

It has also been observed that the low pH culture is accompanied by a fungus, something which has not been observed with higher pH cultures. The fungus has not been identified. We have not ruled out the possibility that a beneficial interaction exists between *Leptospirillum ferrooxidans* and the fungus, contributing to the ability of the bacteria to function in the extremely acid environment. It is hypothesized that the fungus is part of a defense mechanism by the bacteria against the extreme environment in which it exists.

It is therefore felt that *L. ferroxidans* can play an active rcle in the first stage of our process by oxidizing the ferrous iron dissolved from the mineral, as well as that formed during the ferric iron oxidation of the mineral sulphides. In addition, it is likely that the organism also oxidizes some of the pyrite present in the process, producing the ferric iron necessary for the chemical oxidation of the multimetallic sulphides such as arsenopyrite.

We must also consider that *L. ferroxidans* can play a role in the second stage as it is known to oxidize ferrous iron as well as *T. ferrooxidans*.

*T. thiooxidans* uses elemental sulphur as a substrate and is active at highly acidic conditions, such as pH 0.3–1.5. *T. ferrooxidans* uses both sulphides and dissolved ferrous iron as substrates, but cannot oxidize elemental sulphur at low pH values. In the present invention both of these strains have been adapted by continuous culturing techniques to low pH values and high dissolved arsenic concentrations. In some cases we adapted these to operate at pH values as low as 0.3, and arsenic as high as 26.94 g/l.

Our process differs from the prior art in that stage of the multi-stage biological leach uses *T. thiooxidans* as the main leaching organism. During this leach, operated at an Eh of 600–750, preferably 650–720 mV, typically arsenopyrite and pyrite are partially oxidized to elemental sulphur as an intermediary product. This elemental sulphur would normally coat the active mineral surfaces and inhibit further rapid oxidation of the sulphides. However, in our process, the strain of the elemental sulphur oxidizing bacterium, *T. thiooxidans*, rapidly converts the elemental sulphur to sulphate, thereby allowing the oxidation of sulphides to go to completion rapidly. In addition, partial chemical oxidation of iron sulphides such as pyrite and arsenopyrite, by oxygen and ferric sulphate is possible, which also produces elemental sulphur. The bacterium *T. thiooxidans* will also oxidize this chemically produced elemental sulphur rapidly, thus allowing the more rapid conversion of the mineral sulphide into metal sulphate and sulphuric acid.

The oxidizing capability of ferric iron is enhanced by the actions of *T. ferrooxidans*, and *L. ferrooxidans* which rapidly regenerate ferric iron from the ferrous iron produced. When *L. ferrooxidans* is the predominant organism, this oxidation can be carried out at pH values as low as 0.3. The process appears to be applicable to any multi-metallic sulphides that can be oxidized by oxygen or ferric iron and produce elemental sulphur.

The sulphide material is first crushed and ballmilled, if required, to typically 100% minus 200 mesh (Tyler standard screen-scale designation). The finely ground feed is then slurried with water and fed to the first of a series of bioleach reactors which contain a high population of oxidizing microorganisms. Depending on the nature of the material, leaching is carried out at a pulp density typically between 1% and 65% and a pH range of 0.3-2.8. The temperature of leaching should be in the range of 1° C. to 45° C. and preferably 30° C. to 40° C.

Most sulphide materials will have a high enough sulphide content to enable the bacteria to produce sufficient acid to neutralize acid consuming constituents contained in the material; however for those feeds with low sulphide content it may be necessary to provide for the addition of extra acid. Any source of sulphuric acid, not necessarily pure, will suffice.

The leach reactors are agitated by conventional mechanical or air-lift means. Air is blown into the reactors to provide oxygen for the sulphide oxidation reactions and for bacterial growth. Slurry passes from one tank to the next by means of gravity overflow. The number of leach stages required depends on the nature of the feed but will vary from one stage to five stages. A distinct advantage of the process over the prior art is that the chemical/biological leach is so efficient that the retention time is reduced to 1-5 days and as much as 50% or more of the oxygen in the air blown into the reactor is utilized. Slurry exiting the final bioleach reactor undergoes a solid-liquid separation step, and the metals of economic interest are recovered by methods well known in the industry.

In a variation of the process, the material can be treated by conventional heap leach methods, in which case the oxidation step would require 1-12 months to complete but would be much less expensive than mechanical or air agitation methods.

The bacteria require certain nutrients, the most important of which are sources of nitrogen, phosphorus and carbon dioxide. Often the sulphide material itself will contain enough nutrients to sustain activity, but for feeds high in sulphide content it may be advantageous to augment the available nutrient supply with a source of ammonium sulphate and potassium phosphate, which are commonly available as agricultural fertilizers. Amounts sufficient for optimum biological activity are from 0.5-10 kg $(NH_4)_2SO_4$ and 0.1-2 kg $KH_2PO_4$ per tonne feed. Similarly, it is sometimes advantageous to provide minute amounts of carbon dioxide to supplement the carbon dioxide content of the air. Sources of carbon dioxide include the gas which can be injected into the air supply to a concentration of about 0.1%, or any carbonate source such as limestone which will react with acid in the tanks to form $CO_2$.

The progress of the leach can be readily followed by measurement of the Eh of the leach solutions, since the oxidation of elemental sulphur takes place at a lower Eh than the oxidation of sulphides and ferrous iron.

The Eh is a measure of the reduction-oxidation potential of a solution (redox). A higher Eh indicates stronger oxidizing conditions.

Theoretically, the Eh is a function of the pH, the gas constant, the temperature and the quotient of the oxidized species and reduced species. For a pure acidic iron sulphate solution under conditions of standard temperature and pressure, the Eh will be about 680 mV when the amount of ferric iron in solution equals the amount of ferrous iron.

Thus, according to one embodiment of the present invention, one stage of the leach is operated with a mixture of *T. thiooxidans*, *T. ferrooxidans*, and *L. ferrooxidans* at a pH of 2.5 or lower and at an Eh of less than 750 mV. Under these conditions *T. thiooxidans* grows rapidly, probably by oxidizing elemental sulphur. This causes the *T. ferrooxidans* and *L. ferroxidans* which cannot oxidize elemental sulphur rapidly, but are capable of oxidizing ferrous iron, to become secondary organisms. Because the ferric iron is reduced faster than it can be regenerated by *T. ferrooxidans* and *L. ferroxidans*, the leach progresses at the relatively low Eh of 600-750 mV. Because most of the multimetallic sulphides are removed in the first stage of the leach, one or more later stages of the leach operate at an Eh of typically 750 mV or more, because *T. ferrooxidans* is the predominant microorganism, oxidizing pyritic sulphide and dissolved ferrous iron. The resultant dissolved ferric iron can then, through pH control, be precipitated as basic ferric sulphate. This compound does not interfere with the leaching process. It can be readily separated from the leach suspension by gravitational settling, and can be disposed of safely in a tailings pond.

Since ferric iron is an effective oxidant for sulphide minerals, it is an advantage of the present invention that the leach can be operated at pH values as low as 0.3, conditions at which ferric iron is 10-100 times more soluble than it is at pH 2.3.

An important advantage of the invention is that in the case of arsenopyrite, under the highly oxidative conditions of the later stage of the leach, the dissolved 3-valent arsenic, which is a potential pollutant, will be oxidized to its 5-valent form and precipitated as ferric arsenate, an environmentally safe waste product that can be easily separated from the leach solution and disposed of in a tailings pond without environmental impact. Similar oxidative conditions apply to antimony.

The process of the invention is a continuously operating process utilizing more than one stage. Most of the chemical/biological action using the bacterium *T. thiooxidans* preferably takes place in the first stage, while in the subsequent stages the activity of *T. thiooxidans* is decreased in favour of the activity of the bacteria *T. ferrooxidans* and *L. ferroxidans*, which oxidize the by then more readily available sulphide portion of the pyrite minerals present in most arsenopyrite ores and concentrates.

In a variation of the process, the leach is carried out in a single stage with a sufficient residence time to allow for the initial development of predominantly *T. thiooxidans*, followed by the later development of *T. ferrooxidans* and *L. ferroxidans*.

In our invention, the bacteria *T. ferrooxidans* and *L. ferroxidans* will also rapidly oxidize most of the dissolved ferrous iron to ferric iron which in turn assists in the oxidation of the metal sulphides. In addition, the ferric iron reacts with the arsenate ions to produce the environmentally acceptable ferric arsenate waste product, as well as the equally acceptable basic ferric sulphate or jarosite. When the leach is conducted at a pH of less than 1.3, *L. ferroxidans* is the active iron oxidizer. Each stage may be conducted in a separate reactor. Since the precious metals are normally not finely disseminated in the sulphides, it is an advantage of the process of the invention that in most cases it is not necessary to oxidize all the sulphide material present.

According to the invention, bacterial cultures of *T. thiooxidans*, *T. ferrooxidans* and *L. ferroxidans* used are first adapted to high dissolved arsenic concentrations by subjecting the cultures in a solution containing 1,000 mg/l dissolved arsenic, to successive incremental concentrations of arsenic while operating in a continuous mode. Incremental increases in dissolved arsenic concentration are obtained by increasing the pulp density of the arsenopyrite feed material. The adaptation process is as follows. A culture of the bacteria is inoculated into a 5% by weight suspension of an arsenopyrite concentrate containing 14% arsenic. Once the bacteria have developed through their lag phase, fresh concentrate is added to the suspension on a continuous flowthrough basis so that the solids contents of the suspension remains at 5%, allowing the dissolved arsenic concentration to reach 7,000 mg/L. Subsequently, the solids content of the feed is increased incrementally to as high as 25%, allowing for a three day adaptation time for the bacteria between increases. At the high pulp density, the dissolved arsenic concentration theoretically could reach 35,000 mg/L.

The process of the invention has been demonstrated by operating on a continuous bench scale leach for over 6 months, using these special cultures in a suspension containing 12 g/l dissolved arsenic and 30 g/l iron at a pH of 1.1, to oxidize an arsenopyrite/pyrite mixture.

A distinct difference between the present invention and the prior art is that the prior art refers to the bacterium *T. ferrooxidans* as the sulphide oxidizing organism. This invention employs at least two and possibly three distinctly different bacteria. In the multimetallic sulphide oxidizing stage, the predominant bacterium is a sulphur oxidizer, *T. thiooxidans*, different from *T. ferrooxidans* in that it operates at low Eh and pH values and oxidizes elemental sulphur only and not dissolved ferrous iron. Only in those stages where there is little arsenopyrite substrate left, does *T. ferrooxidans* play a dominant role. or, if the pH is low, does *L. ferroxidans* play a dominant role. Thus the invention employs or emphasizes three different organisms, one an elemental sulphur oxidizer and the other two sulphide/ferrous iron oxidizers. When the amount of acid produced from the oxidation of elemental sulphur causes the pH of the leach solution to fall below 1.3, *L. ferrooxidans* becomes the active iron oxidizer and may also oxidize some of the sulphide present.

Therefore, *T. ferrooxidans* and *L. ferroxidans* differ mainly from *T. thiooxidans* in that the former are capable of oxidizing ferrous iron and the latter is not. In addition, while the former organisms are capable of oxidizing elemental sulphur, only *T. thiooxidans* can do so at pH values below 1.0. *T. ferrooxidans* does oxidize elemental sulphur at pH values above 1.0, but relatively slowly compared with *T. thiooxidans*. The elemental sulphur oxidizing capabilities of *L. ferroxidans* is supposed to be zero, but we have not carried out any tests to confirm this.

The process is applicable to those multimetallic sulphide materials which form elemental sulphur during oxidative leaching. These include, but are not limited to, sulphide materials containing the minerals pyrite, arsenopyrite, pyrrhotite, tetrahedrite, chalcopyrite, sphalerite, millerite and cobaltite.

The mixed cultures have been identified by taxonomy studies, and are described below.

The mixed cultures, arsenic resistant and low pH resistant cultures have been deposited in the following culture collection:
American Type Culture Collection
12301 Parklawn Drive
Rockville, Md.
U.S.A.

(1) Mixed Culture, Coded GBB mixed ATCC No. 53,618.

This culture contains *T. thiooxidans*, *T. ferrooxidans*, and *Leptospirillum ferrooxidans*. The culture is effective at normal pH ranges of about pH 1.3 to 2.8, but is also effective at lower pH, such as below 1.

(2) Low pH Resistant Culture—coded GBB from ATCC No. 53,625

This culture contains mainly *Leptospirillum ferrooxidans*, as well as some *T. ferrooxidans* . It is capable of oxidizing ferrous iron at low pH, below 1. This culture is particularly useful when treating strong acid producing materials amenable to ferric iron oxidation.

(3) High Arsenic Resistant Culture—Coded GBB Sulfur

This culture is an arsenic resistant *T. thiooxidans*, ATCC 53,619. This culture is unique for its arsenic resistance and can be used for the leaching of elemental sulphur produced during the leaching of multimetallic sulphides such as arsenopyrite.

These cultures have also been deposited with:
Olli H. Tuovinen, Ph.D.
Professor of Microbiology
The Ohio State University
Department of Microbiology
484 W. 12th Avenue
Columbus, Ohio U.S.A.

Thus, the above cultures can be used, at normal pH with a lower limit of 1.3, to oxidize multimetallic sulphides utilizing *T. thiooxidans* and *T. ferrooxidans*. By utilizing *L. ferroxidans*, the mixed culture can be used to oxidize multimetallic sulphides at pH values below 1, and as low as 0.3. When the mixed cultures are made up from arsenic resistant strains, arsenic containing multimetallic sulphides can be leached. The culture of *L. ferrooxidans* can be used to oxidize pyrite and similar sulphides under highly acidic conditions. In addition, the arsenic resistant strains can be used, individually or collectively, to oxidize arsenic containing sulphides.

The bacterial cultures are further characterized as follows:

Mixed Mineral Leaching Bacteria—GBB Mixed

This culture is a mixture of acidophilic bacteria capable of growing with arsenopyrite as the sole source of energy. The culture is aerobic and utilizes carbon dioxide as the source of carbon. The major important properties of the mixed culture are (1) the ability to oxidize arsenopyrite for energy and growth; (2) the ability to oxidize ferrous iron for energy and growth, due to the presence of *Thiobacillus ferrooxidans* and *Leptospirillum ferrooxidans* types of bacteria; and (3) the ability to oxidize elemental sulfur at and below pH 1.0 due to the presence of *Thiobacillus thiooxidans* type of bacteria. Two cultures derived from this mixed culture by utilizing ferrous sulfate and elemental sulfur as the respective substrates have been submitted to the ATCC as separate depositions. However, the optimum composition of the mixed culture is best realized by maintaining the mixed culture in arsenopyrite-containing liquid media.

The mixed culture is maintained in shake flasks at room temperature in a mineral salts medium. The following medium is used for routine cultivation.

| | |
|---|---|
| $(NH_4)_2SO_4$ | 3.0 g/liter |
| KCl | 0.1 g/liter |
| $K_2HPO_4$ | 0.5 g/liter |
| $MgSO_4.7H_2O$ | 0.5 g/liter |
| $Ca(NO_3)_2$ | 0.01 g/liter |

Use sulfuric acid to adjust to pH 2.0. The mineral salts solution can be autoclaved or filter-sterilized. After sterilization, add aseptically finely ground arsenopyrite as the substrate (20 g/100 ml). Because arsenopyrite is not commercially available, a sample of about 200 g is enclosed with this culture deposition. Other arsenopyrite as well as pyrite concentrate materials may also be suitable if they are finely ground to provide a large surface area as suspended solids in the final medium.

An active culture releases iron and arsenic into solution during arsenopyrite oxidation and produces sulfuric acid because of the usual presence of pyrite. An actively growing culture lowers the pH to below 1.0 during the incubation; normally this will occur in eight to twelve days with a 7.5% (vol/vol) inoculum in batch culture. Microscopic examination of the culture initially and during the incubation may also be used to verify increases in cell numbers.

It should be noted that many commercially available pH probes display poor linearity in the pH 0.5-2.0 range. It is necessary to calibrate the pH meter with both pH 1.0 and pH 2.0 buffer solutions for accurate measurements. In the event of poor linearity, intermediate pH values of sample solutions should be checked against a calibration buffer that has the closest pH value (i.e., pH 1.0 or pH 2.0). STORAGE: Store under liquid nitrogen.

Mixed Mineral Leaching Bacteria—GBB Iron

This culture contains ferrous ion oxidizing acidophilic bacteria, specifically characterized by their ability to grow at pH 0.9 with ferrous sulfate as the sole source of energy. The culture is aerobic and utilizes carbon dioxide as the source of carbon. The culture resembles *Leptospirillum ferrooxidans* in its morphological characteristics and in its ability to grow with ferrous ion as the energy source, but is differentiated from previously described *L. ferroxidans* cultures by its ability to grow at pH 0.9. The *L. ferroxidans* type is the predominant morphological form in the culture. Additionally, the culture contains as a minor component short straight rods which resemble the morphological description of *Thiobacillus ferrooxidans*. Again, the straight rod shaped cells are uniquely different from previous descriptions of *T. ferrooxidans* due to the pH 0.9 growth conditions. Filamentous fungi of unknown taxonomic status are also present in this culture. These fungi tend to form small suspended pellicles of white-greyish color.

The culture is maintained in shake flasks at room temperature in a mineral salts medium. The following medium is used for routine cultivation:

| | |
|---|---|
| $(NH_4)_2SO_4$ | 3 g |
| KCl | 0.1 g |
| $K_2HPO_4$ | 0.5 g |
| $MgSO_4.7H_2O$ | 0.5 g |
| $Ca(NO_3)_2$ | 0.01 g |
| $FeSO_4.7H_2O$ | 44.22 g |
| Distilled water | 1000 ml |
| 12 N $H_2SO_4$ | 28 ml | Final pH 0.9 |

The medium can be filter-sterilized or it can be prepared in separate portions as follows: (i) ferrous sulfate dissolved in distilled water acidified with sulfuric acid (filter-sterilize), and (ii) minerals salts dissolved in distilled water (autoclave). The size of the inoculum is usually 7.5% (vol/vol). Growth of the culture can be monitored by any of the following methods: (i) microscopic examination of the cell density; (ii) determination by chemical methods of the residual ferrous ion; and (iii) measurement of the redox potential of the culture.

NOTE 1. Fully grown cultures should be transferred to fresh media within 3 to 4 days to avoid cell death and prolonged lag periods. Note 2. Many commercially available pH probes display poor linearity in the low pH range required for calibration of the pH meter. The pH meter should be calibrated with pH 1.0 buffer solution and the final pH of each batch of media should be determined to ensure the desired pH.

STORAGE: Store under liquid nitrogen.

Mixed Mineral Leaching Bacteria-GBB Sulphur

This culture contains sulfur-oxidizing, arsenic resistant, acidophilic bacteria, specifically characterized by their ability to grow at pH 1.0 with elemental sulfur as the sole source of energy. The culture is aerobic and utilizes carbon dioxide as the source of carbon. The culture resembles *Thiobacillus thiooxidans* in its general characteristics and has been specifically derived from a mixed culture of bacteria previously maintained under selective conditions in arsenopyrite-containing mineral leaching suspensions. The parent mixed culture has been deposited at the same time with the ATCC ("Mixed Mineral Leaching Bacteria, GBB Mixed ATCC No. 53618").

The culture is maintained in shake flasks at room temperature in a mineral salts medium. The following medium is used for routine cultivation.

| | |
|---|---|
| $(NH_4)_2SO_4$ | 3.0 g/liter |
| KCl | 0.1 g/liter |
| $K_2HPO_4$ | 0.5 g/liter |
| $MgSO_4.7H_2O$ | 0.5 g/liter |
| $Ca(NO_3)_2$ | 0.01 g/liter |
| $FeSO_4.7H_2O$ | 0.02 g/liter |

Use sulfuric acid to adjust to pH 1.0. The mineral salts solution can be autoclaved or filter-sterilized. After sterilization, add aseptically precipitated sulfur (flowers of sulfur) as the substrate (1-4g/100 ml). The sulfur is steam-sterilized three times for 30 min each during three consecutive days. Growth of the culture can be monitored by microscopic examination of the cell density and by measurement of the pH during incubation. The size of the inoculum is 7.5% (vol/vol). NOTE: Many commercially available pH probes display poor linearity in the pH 0.5-1.0 range. It is necessary to calibrate the pH meter with pH 1.0 buffer solution and check the calibration against pH 2.0 buffer solution for accurate measurements.

STORAGE: Store under liquid nitrogen.

Another advantage of this invention is that when the invention is used for the solubilization of refractory sulphides containing precious metals, liberation of the precious metals can often be accomplished by only partial oxidation of the sulphides.

The following examples illustrate the invention:

EXAMPLE ONE

A mixed pyrite-arsenopyrite concentrate received from the Giant Yellowknife Mine at Yellowknife, Northwest Territories, Canada, was processed through a bench scale continuous bioleach circuit over 10 months to develop an arsenic-resistant strain of bacteria and evaluate the process of the invention for this concentrate.

The as-received concentrate was re-milled to 90%-400 mesh and assayed 18.6% Fe, 5.9% As, 15.0% $S^{2-}$, 74 g/t Au and 28 g/t Ag. Concentrate in a feed tank was slurried to the desired pulp density with water and bacterial nutrient salts which consisted of 10kg $(NH_4)_2SO_4$/t conc. and 1 kg $KH_2PO_4$/t conc.

The bioleach circuit consisted of three 5 liter capacity turbine agitated tanks connected in series, with pulp pumped from one tank to the next with peristaltic pumps. Air enriched with 1% $CO_2$ was sparged in directly underneath the tanks to provide oxygen for sulphide oxidation and bacterial growth. Carbon dioxide enriched air was not essential, but the extra $CO_2$ did appear to decrease the bacterial adaptation times required, and improve leach rates by 20-30%. Tank temperature was controlled at 35° C.

To start the bacterial adaptation process, each of the three leach tanks was inoculated with an active mixed culture containing *T. ferrooxidans*, *T. thiooxidans*, and *L. ferroxidans*. The circuit was left in batch mode for 3 days to allow the bacteria to grow and multiply, at which time slurried feed containing 100 g/l concentrate and bacterial nutrients were pumped slowly—at a rate of 50 ml/h—to the first reactor in the bioleach circuit. Simultaneously, tank 1 contents were pumped at the same rate to tank 2, tank 2 contents to tank 3, and tank 3 contents to a product tank.

Over the course of the next month, the feed rate was gradually increased incrementally until a rate of 110 ml/h, corresponding to a retention time of 45 hours per tank, was reached. Successful adaptation was evident when bioleach rates were observed to increase in direct proportion to the increase in feed rate.

After a feed rate of 110 ml/h had been successfully achieved, the feed pulp density was increased gradually, in increments of 2 g/l, until a pulp density of 200 g/l had been reached. Again successful adaptation was indicated by bioleach rates increasing in direct proportion to the increase in pulp density. Soluble arsenic concentrations of 12 g/l were attained without any adverse effects on the adapted bacteria.

Three distinctly different strains of bacteria were identified in each tank; *Thiobacillus thiooxidans* which oxidizes only elemental sulphur, and *Thiobacillus ferrooxidans* and *Leptospirillum ferrooxidans* which oxidize primarily pyrite and ferrous iron, and to a lesser extent, elemental sulphur.

Once steady state leach conditions had been achieved at 200 g/l solids and 110 ml/h flow rate, slurry was removed from each tank, filtered and the solids retained for analysis and cyanidation testing. Sulphide analyses revealed that sulphide extractions (cumulative) achieved in the bioleach circuit were: tank 1-57.9%; tank 2-89.6%; tank 3-91.5%. The solids also contained some elemental sulphur; tank 1-1.1% $S^o$; tank 2-1.9% $S^o$, tank 3-1.5% $S^o$.

The bioleachate exiting the last leach tank contained 30.0 g/l iron (as $Fe^{3+}$), 11.3 g/l arsenic (as $As^{5+}$), and registered a pH of 1.1 and an Eh of 813 mV, whereas the Eh of the solution in the first tank was only 720 mV. This low pH showed that *L. ferroxidans* played a dominant role in the oxidation processes taking place in the last tank.

Solids weight loss was 40.2%. The bioleachate was neutralized to pH 4.0 with limestone and then further neutralized to pH 6.5 with lime. This procedure ensured that all arsenic precipitated as ferric arsenate, with excess iron precipitated as jarosite and excess sulphate as gypsum. After filtration to remove the tailings for disposal, the treated bioleachate and make-up water was recycled back to the feed tank.

Solids exiting the last leach tank assayed 6.9% Fe, 1.0% As, 2.1% $S^{2-}$, 9.65% $SO_4^{-2}$, 110 g/t Au and 38 g/t Ag. Based on solids and solution assays, iron extraction was 81% and arsenic extraction was 95%. Some oxidized iron had re-precipitated as jarosite during the leach and remained with the solids.

The untreated head concentrate and solids from each tank underwent standard 24h bottle-roll cyanidation testing. The results are summarized below.

|  | Head Conc. | Tank #1 | Tank #2 | Tank #3 |
|---|---|---|---|---|
| CN Tail Assays |  |  |  |  |
| Au, g/t | 41.56 | 6.31 | 2.47 | 2.77 |
| Ag, g/t | 8.91 | 9.26 | 16.80 | 17.49 |
| Extractions (%) |  |  |  |  |
| Au | 36.8 | 92.8 | 98.1 | 97.5 |
| Ag | 55.9 | 64.1 | 61.5 | 50.2 |

For a control test, a sample of the same finely ground concentrate was bioleached in batch mode at a pulp density of 200 g/l. The test was inoculated with a culture of *T. ferrooxidans* previously grown batch-wise on Giant Yellowknife feed. Because the culture had not originated from a prolonged continuous run, which allows development of both *T. ferrooxidans* and *T. thiooxidans*, only *T. ferrooxidans* was present.

After 14 days, leaching of iron and arsenopyrite had stopped, with only 26.7% iron and 75.8% arsenic oxidation achieved. The bioleachate registered a pH of 1.58 and an Eh of only 650 mV. We believe leaching stopped prematurely because of the inability of *T. ferrooxidans* to oxidize elemental sulphur at a rate fast enough to prevent So from coating the sulphide minerals. In contrast, when leaching in continuous mode, both *T. ferrooxidans* and *T. thiooxidans* develop with the latter oxidizing $S^o$ and allowing oxidation of the sulphides to go to completion.

EXAMPLE TWO

Two tonnes of a mixed pyrite-arsenopyrite concentrate, received from the Campbell Red Lake Mine in Balmerton, Ontario, Canada, were processed through a pilot plant. Conventional cyanide treatment of the concentrate typically achieved only 60-70% gold extraction and 50-70% silver extraction; therefore Campbell Red Lake pretreats the concentrate by roasting to enhance gold recovery to 97%.

The concentrate was re-milled to 90%-400 mesh and assayed 22.5% Fe, 6.9% As, 15.7% $S^{2-}$, 122 g/t Au and 33 g/t Ag. Concentrate was slurried to 17.5% solids (200 g/l) with treated recycled bioleachate and make up water in a feed tank. About 10 kg $(NH_4)_2SO_4$/t conc. and 1 kg $KH_2PO_4$/t conc. were added as nutrients for the bacteria.

Slurried feed was pumped continuously to the first reactor in the bioleach circuit at a rate of 3.73 lh (0.75 kg solids/h). The leach circuit consisted of three 167 liter capacity, turbine agitated tanks connected in series with pulp passing from one tank to the next by gravity overflow. Retention time was 45 hours per tank for a total leach residence time of 135 hours. Each tank contained a mixture of three distinctly different strains of bacteria, *Thiobacillus ferrooxidans* and *Thiobacillus thiooxidans*, and *L. ferroxidans*. Air was sparged in directly underneath the turbines to provide oxygen for sulphide oxidation and bacterial growth. Tank temperature was controlled at 35° C., although temperatures as high as 42° C. presented no problems for the bacteria.

Measurement of the sulphide contents of solids extracted from each leach tank indicated that cumulative sulphide oxidations achieved were 48.3% in tank 1, 75.3% in tank 2 and 93.5% in tank 3. In addition, 1.0-1.5% So was present in each case. Minimum oxygen utilizations achieved were 55% in tank 1, 35% in tank 2 and 30% in tank 3.

Product exiting the last tank contained 147 g/l solids, representing a solids weight loss of 26.5%. The solids assayed 8.3% Fe, 0.9% As, 1.4% $S^{2-}$, 16.35% $SO_4^{2-}$, 170 g/t Au and 39 g/t Ag. The solution registered a pH of 1.45 and Eh of 796 mV, whereas the Eh of the solution in the first tank was 700 mV. The solution in the last tank contained 32.8 g/l Fe, 12.6 g/l As, 79.0 g/l $SO_4$, 1.8 g/l Mg, 0.7 g/l Ca and trace amounts of Cu, Co, Ni and Zn. Iron was present totally as $Fe^{3+}$ and arsenic solely as $As^{5+}$. Based on solid solution assays, 72% iron, 89% arsenic and 71% sulphur dissolution was achieved. A substantial portion of the oxidized iron and sulphur had re-precipitated as jarosite.

The head sample and unwashed solids from each tank underwent standard 24 hour bottle-roll cyanidation testing. Results are summarized below.

|  | Head Conc | Tank #1 | Tank #2 | Tank #3 |
| --- | --- | --- | --- | --- |
| CN Tail Assays |  |  |  |  |
| Au, g/t | 10.1 | 8.88 | 4.66 | 3.50 |
| Ag, g/t | 15.6 | 18.17 | 17.14 | 13.37 |
| Extractions (%) |  |  |  |  |
| Au | 65.0 | 92.0 | 96.2 | 98.0 |
| Ag | 60.0 | 47.7 | 54.8 | 65.8 |

Product bioleachate exiting the last reactor was neutralized to pH 4.0 with slurried limestone, and further neutralized to pH 6.5 with slurried lime. After thickening, the solution was recycled back to the feed tank, and the solids, which contained gypsum jarosite and ferric arsenate, were disposed of as tailings.

EXAMPLE THREE

A mixed pyrite-arsenopyrite ore from the Lander County area of Nevada was treated by the process using conventional heap leach methods. The ore assayed 3.97% iron, 1.33% arsenic, 3.52% sulphide sulphur and 7.10 grams per tonne gold. Standard cyanide bottle-roll leach tests on finely pulverized ore (minus 200 mesh) demonstrated that only 18.7% of the gold could be extracted. The remainder of the gold was presumably encapsulated within the sulphide minerals, and therefore not amendable to cyanide extraction.

A 3.0 kg sample of the ore was crushed to minus 0.64 cm and packed into a 7 cm diameter by 84 cm long plastic column. The solution application system consisted of a reservoir bucket holding 3-4 liters solution, a peristaltic pump, and a discharge bucket. Solution was pumped from the reservoir through the column at a rate of 10 liters per hour per square meter cross-sectional area, and allowed to collect in the discharge bucket. After each 3-4 day leach cycle, discharged solution was returned to the reservoir bucket and water added to compensate for evaporation. The leach cycle was then repeated.

The column was initially saturated with water and the water uptake volume was recorded. The test was then acidified by adding sulphuric acid to the reservoir bucket and pumping acidified water through the column until the pH had stabilized at 2. The column was then inoculated with a mixed culture which had previously been adapted to the same, finely ground, ore. Leach progress was monitored by sampling leachate on a weekly basis and measuring soluble iron, arsenic, pH and Eh.

The ore was leached for 130 days. The Eh remained below 740 mV for the first 90 days, after which it increased ultimately to 890 mV by the end of the leach. The pH decreased from 2.0 to 1.41 during the course of the leach. Iron and arsenic extractions achieved were 65.5% and 86.4% respectively. Sulphide oxidation achieved was 45.9%.

After the bioleach treatment, the ore was washed and brought to a pH of 10.9 by pumping a weak lime solution through the column. The ore was then cyanide leached for 27 days. Gold recovery based on a calculated head gold content of 7.38 g/t was 82.0%. Thus the process, using heap leach methods, improved gold recovery from 18.7% to 82.0%.

EXAMPLE FOUR

Cultures of bacteria from the first and last reactors of a 3-reactor leaching process as described in Ex. 1 were grown on pyrite, and elemental sulphur. The latter substrate was at pH 0.9.

On pyrite substrate, a rapid and consistent drop in solution pH and increase in Eh was noted in the test containing the culture from the last reactor, but no acid was produced with the culture from the first reactor, indicating that it was not capable of oxidizing sulphides, and therefore contained predominantly *T. thiooxidans*.

On elemental sulphur substrate both cultures indicating that *T. thiooxidans* was present and active in both reactors.

These results indicate that the bacterium *T. thiooxidans* is present in all reactors, but predominates in the first reactor where it exists on the oxidation of elemental sulphur which is produced from the chemical reaction of arsenopyrite with ferric iron and oxygen. Elemental sulphur removal in the first reactor by *T. thiooxidans* is rapid enough to ensure substantially complete chemical oxidation of the arsenopyrite. A portion of the resultant elemental sulphur passes into the subsequent reactors, providing a continuing source of substrate for *T. thiooxidans*.

Although *T. ferrooxidans* is present in all reactors, it predominates in the last reactor where it oxidizes pyrite and ferrous iron.

EXAMPLE FIVE

A culture grown on an arsenopyritic concentrate at a pH of 0.28 was grown successfully on ferrous iron at pH 0.9 and 2.3 as well as on elemental sulphur at pH 0.9. It must therefore be concluded that the culture contained both *T. thiooxidans* and a special bactyerial strain capable of oxidizing ferrous iron at extreme low pH values. This special strain was identified by visual observation to be *Leptospirillum ferrooxidans*.

EXAMPLE SIX

A culture of bacteria was grown on a arsenopyritic concentrate containing 37.48% iron and 3.90% arsenic. Using a suspension containing 40% w/w solids, numerous serial transfers were carried out, ultimately producing a culture active in a solution of pH 0.5, containing 26.94 g/l dissolved arsenic and 89.76 g/l dissolved iron.

When samples of this culture were grown on ferrous iron at pH 0.9, it oxidized the ferrous iron rapidly. It also oxidized elemental sulphur at pH 0.9 and oxidized ferrous iron at pH 2.3, proving that it contained *Leptospirillum ferrooxidans*, *Thiobacillus thiooxidans* and *Thiobacillus ferrooxidans*.

EXAMPLE SEVEN

The process has been tested on a large scale at Giant Yellowknife's Salmita gold mill in the Northwest Territories, Canada. The plant was operated for demonstration purposes only and ran successfully for a six week period.

The bioleach section of the plant consisted of four 3.05 m diameter by 3.43 m high stainless steel tanks, air sprayed and agitated by overhead stirrers. Temperature in each tank was controlled at 35° C. by the flow of hot or cold water through cooling coils inserted in each tank.

The plant treated a refractory gold ore assaying 0.76% $S^2-$2.68% Fe, 0.73% As and 23 g/t Av. For the final two weeks of operation, the plant processed the ore at a rate of 9.5 tonne/day. Retention time was 2.5 days, pulp density was 23% (w/w). The ore was ball-milled to 80% minus 200 mesh before leaching.

Gold recovery by cyanidation of the untreated ore was typically 65-75%. After bioleaching, gold recovery was consistently 90-95%.

This example demonstrates that the process does work on a larger scale; a size approaching commercial.

While the present invention has been particularly described with reference to certain specific embodiments thereof it will be understood that various modifications may be made to the process by persons skilled in the art without departing from the spirit and scope of the invention. It is intended therefore that this invention be limited only by the claims which follow.

REFERENCES

1. Buchanan, R. E. and N. E. Gibbons, 1974. *Bergey's Manual of Determinative Bacteriology*. The Williams and Wilkins Co., Baltimore. 1268 pp.
2. Tuovinen, O.H. and D.P. Kelly. 1973. Studies on the growth of *Thiobacillus ferrooxidans*. I. *Arch. Microbiol.* 88:285–298.
3. Lui, Ming-shen. 1973. Oxygen transfer in a fermentor. Ph.D. thesis, Dept. Chem. Eng. U.B.C.
4. Tomizuka, N. M., Yagisawa, J., Somaya and Y. Takahara. 1976. Continuous leaching of uranium by *Thiobacillus ferrooxidans Agri. Biol. Chem.* 40(5):1019–1025.
5. Golomzik, A. I. and V. I. Ivanov. 1964. Adaptation of *T. ferrooxidans* to increased hydrogen ion and iron concentrations. *Mikrobiologya* 34 No. 3:465–468.
6. Bruynesteyn, A., Vizsolyi, A. and R. Vos. 1980. The effect of low pH on the rate of ferrous iron oxidation by *Thiobacillus ferrooxidans*. Presented at the conference: *Use of microorganisms in Hydrometallurgy*, Pecs, Hungary.
7. Bruynesteyn, A. and A. Vizsolyi. 1981. The effect of pH and Eh on the chemical and biological leaching of a pyritic uranium ore. *2nd SME-SPE International Solution Mining Symposium*, Denver, Colorado.
8. Groudev, S. N. 1983. Participation of Thiobacillus thiooxidans in the leaching of metals from sulphide minerals. Presented at: *Fifth International symposium on Biohydrometallurgy*, Cagliari, Italy.
9. Norris, P. R. 1983. Iron and Mineral oxidation with leptospirillum-like bacteria. Presented at: *Fifth International Symposium on Biohydrometallurgy*, Cagliari, Italy.
10. Brown, J. E., Luong, H. V. and J. M. Forshaug. 1982. The occurrence of *Thiobacillus ferrooxidans* and arsenic in subarctic streams affected by gold-mine drainage. *Arctic* 35 No.3:417–421.
11. E.Livesey-Goldblatt, Philippe Norman, P. and D. R. Livesey-Goldblatt. "Gold recovery from Arsenopyrite/-pyrite ore by Bacterial Leaching and Cyanidation". Presented at *Fifth International Symposium on Biohydrometallurgy*, Cagliari, Italy.
12. Karavaiko, G. I., Chuchalin, L. K. and T. A. Pivovarova. 1985. Microbiological leaching of metals from arsenopyrite containing concentrates. Presented at: *Sixth International Symposium on Biohydrometallurgy*, Vancouver, Canada.
13. General Mining Corporation. "Plasmid vectors resistant to arsenic-capable of replication in *Thiobacillus ferrooxidans*". RSA No. 8406735.
14. D. A. Rawlings, I. Pretorius and D. R. Woods. 1984. "Expression of a *Thiobacillus ferrooxidans* origin of replication in *Escherichia coli*", *J. of Bacteriology*, Vol. 158, No. 2:737–738.

We claim:

1. A process for oxidizing multi-metallic arsenic and sulphide-containing ores, the process comprising:
   contacting the arsenic containing ore with a leach solution containing a mixed culture containing at least *Thiobacillus thiooxidans, Leptospirillum ferrooxidans* and *Thiobacillus ferrooxidans* in the first stage, at an Eh of less than 750 mV; and
   contacting the products from the first stage with a leach solution containing a mixed culture containing at least *Thiobacillus thiooxidans, Leptospirillum ferrooxidans* and *Thiobacillus ferrooxidans* in a second stage, operated at an Eh of 750 mV or more.

2. A process as claimed in claim 1 in which the ore contains arsenopyrite.

3. A process as claimed in calim 1, in which the ore contains pyrite and other multi-metallic sulphides which produce elemental sulphur during chemical leaching.

4. A process as claimed in claim 1, including a preliminary step of milling the ore to facilitate rapid bacterial action.

5. A process as claimed in claim 1, including supplying the oxygen required for the chemical and biological oxidation for each stage by sparging air or oxygen.

6. A process as claimed in claim 5, in which the air is enriched with carbon dioxide.

7. A process as claimed in claim 6, in which the carbon dioxide is supplied in the form of carbonate in solution.

8. A process as claimed in claim 1, in which the temperature of the leach solutions is controlled in the range of 1°–45° C.

9. A process as claimed in claim 1, in which the temperature of the leach solutions is controlled in the range of 30°–40° C.

10. A process as calimed in calim 1, in which the temperature of the leach solutions is controlled in a range of 5°–50° C.

11. A process as claimed in claim 1, in which the pH of the leach solutions is maintained in the range of 1.3–2.8.

12. A process as claimed in claim 1, in which the leach solutions are treated to maintain their dissolved arsenic concentration at less than 5 g/l.

13. A process as claimed in claim 1, in which the mixed culture of bacteria used is resistant to pH values as low as 0.3, to dissolved arsenic concentrations as high as 27 g/l and to dissolved iron concentrations as high as 100 g/l.

14. A process as claimed in claim 1, in which the pH of the leach solutions is maintained in the range of 0.3–2.8.

15. A process as claimed in claim 1, in which the pH of the leach solution is maintained in the range of 0.3–1.5.

16. A process as claimed in claim 1, including a preliminary step of bacterial adaptation.

17. A process as claimed in calim 16, in which the bacterial adaptation comprises placing the slurry of the ore to be treated in a plurality of bioleaching tanks;

introducing into each tank active mixed cultures containing at least *Thiobacillus ferrooxidans* Leptospirillum ferrooxidans and *Thiobacillus thiooxidans*, allowing the bacteria to develop under stable conditions; then feeding a slurry of ore and nutrients to the first tankl;

pumping the contents of each tank to a subsequent tank, the content of the last bioleaching tank being pumped to a product tank; and gradually increasing the pulp density of the feed until adaptation of the bacteria is complete.

18. A process as claimed in claim 17, in which the two stages each consist of one to five bioleaching tanks.

19. A process as claimed in calim 17, in which the pH of the product from the last bioleach tank is increased to at least 3.5.

20. A process as claimed in claim 17, in which the leach solutions are treated with a neutralizing agent to maintain their pH at 1.3 or higher.

* * * * *